United States Patent [19] [11] Patent Number: 4,913,704
Kurimoto [45] Date of Patent: Apr. 3, 1990

[54] DISPOSABLE INDWELLING CATHETER PLACEMENT UNIT INTO THE BLOOD VESSEL

[75] Inventor: Munehito Kurimoto, Iwata, Japan

[73] Assignee: Sherwood Medical Company, St. Louis, Mo.

[21] Appl. No.: 263,979

[22] Filed: Oct. 26, 1988

Related U.S. Application Data

[63] Continuation of Ser. No. 937,161, Dec. 2, 1986, abandoned.

[30] Foreign Application Priority Data

Dec. 6, 1985 [JP] Japan ................................. 60-274573

[51] Int. Cl.$^4$ ................................. A61M 5/00
[52] U.S. Cl. ..................... 604/171; 604/160
[58] Field of Search ................. 604/158–170, 604/171

[56] References Cited

U.S. PATENT DOCUMENTS

| Re. 31,855 | 3/1985 | Osborne | 604/161 |
| 3,825,001 | 7/1974 | Bennet et al. | 604/171 |
| 4,392,853 | 7/1983 | Muto | 604/171 |
| 4,449,973 | 5/1984 | Luther | 604/161 |
| 4,581,025 | 4/1986 | Timmermans | 604/160 |
| 4,655,750 | 4/1987 | Vaillancourt | 604/171 |

FOREIGN PATENT DOCUMENTS 7408497 10/1975 France ................................. 604/161

Primary Examiner—Barry S. Richman
Assistant Examiner—T. J. Wallen
Attorney, Agent, or Firm—Andrew J. Beck; Montgomery W. Smith; Richard D. Allison

[57] ABSTRACT

A disposable indwelling catheter placement unit includes a transparent plastic catheter for insertion into a blood vessel having depth indicating graduations thereon. The catheter is freely slidable into a transparent plastic tubular sheath having a slit line there along. The unit has a transparent inserter having an inner tube connected to a front portion of the inserter. The sheath tube is releasable from around the catheter responsive to movement through the inserter. By pushing the sheath tube forward into the inserter with the fingers while holding the inserter with other fingers, or pulling the split sheath from the inserter, the catheter can be pushed into the blood vessel up to a desired depth while maintaining sterility.

13 Claims, 4 Drawing Sheets

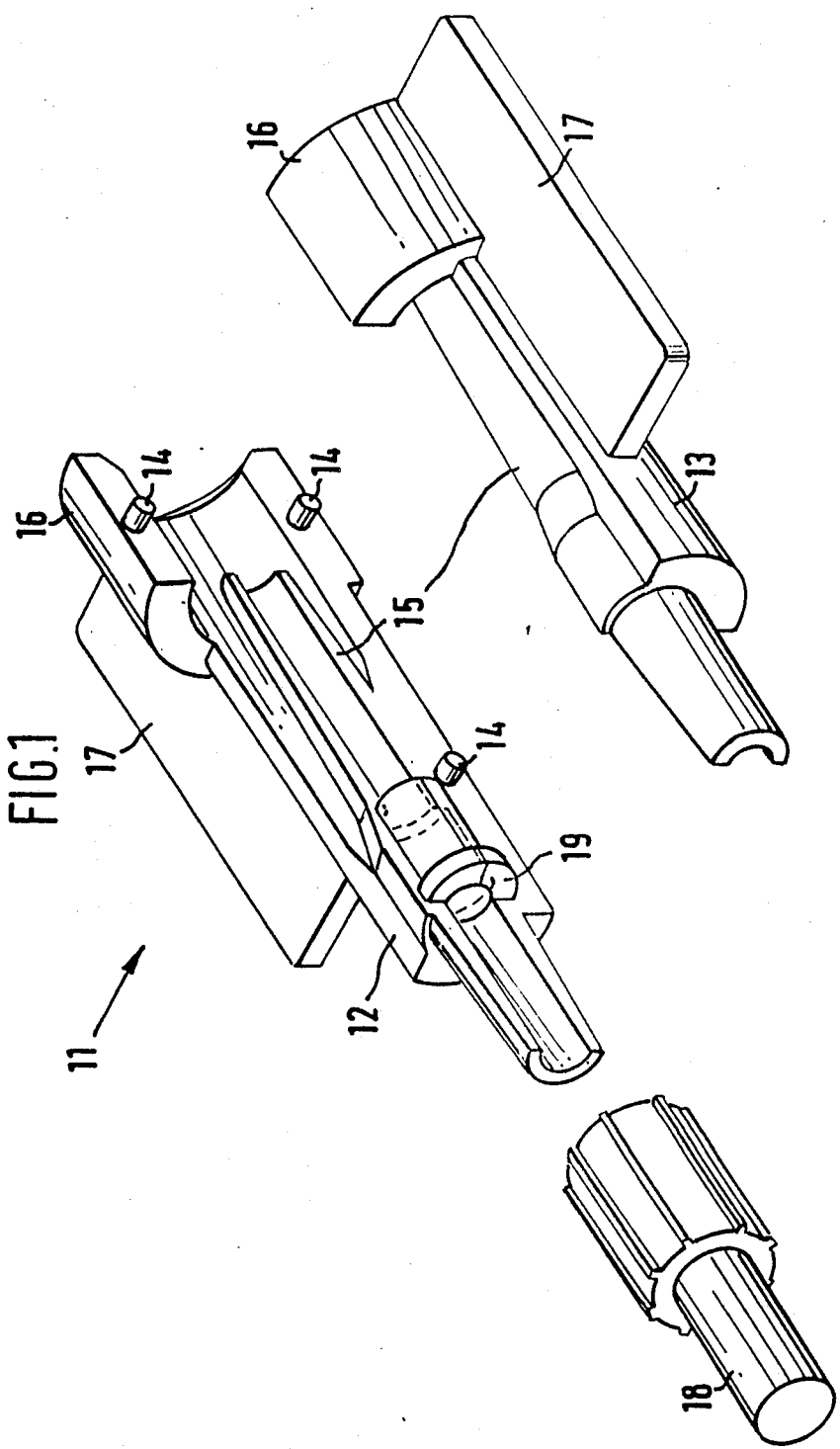

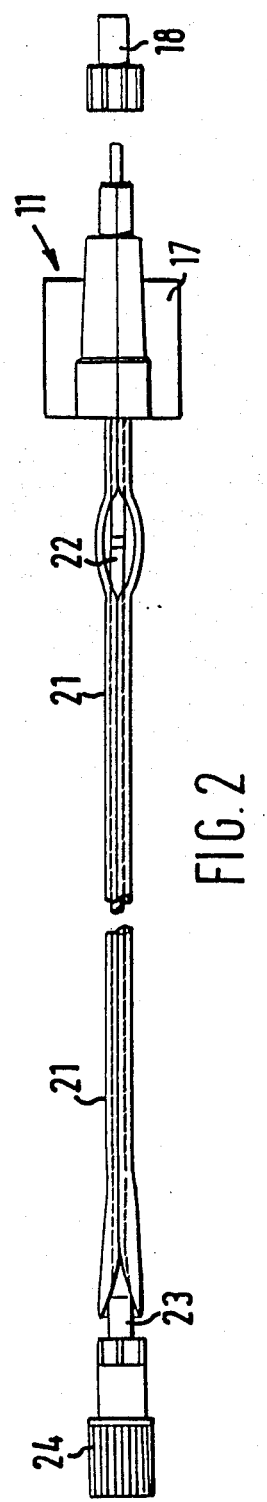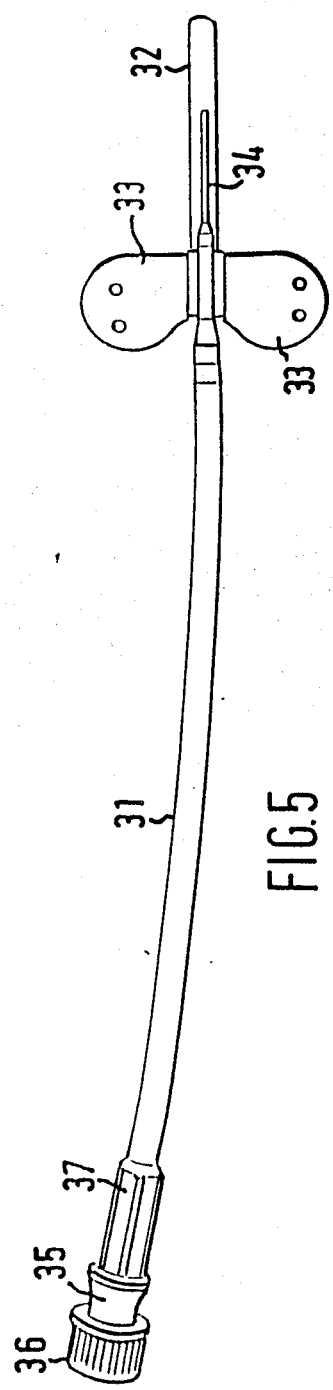

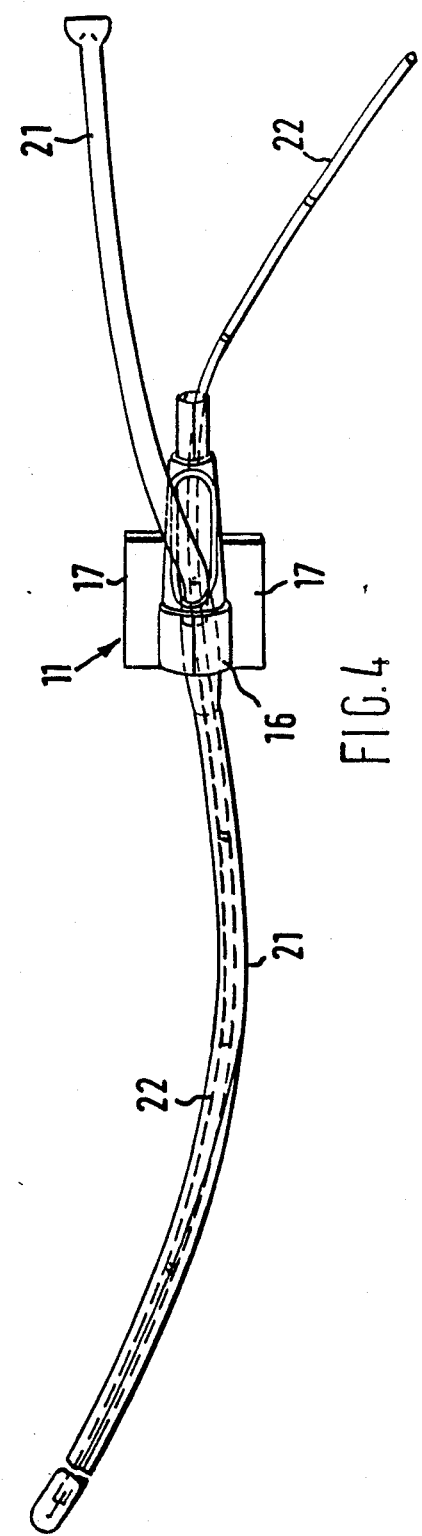

DISPOSABLE INDWELLING CATHETER PLACEMENT UNIT INTO THE BLOOD VESSEL

This a continuation of co-pending applicaton Ser. No. 937,161 filed on Dec. 2, 1986, now abandoned.

BACKGROUND OF THE INVENTION

1. Field of the Invention

The present invention relates to a disposable indwelling catheter placement unit for insertion of a catheter into a blood vessel; and more particularly relates to a unit for indwelling a lengthy catheter into the blood vessel in the vicinity of the heart of a patient up to a desired depth therein and in a sterile manner.

2. Description of Relevant Art

Various improvements have hitherto been attempted to place a catheter made of a plastic tube into the blood vessel of a patient by inserting a tubular needle for the purpose of introducing the catheter as, for example, disclosed in published Japanese Patent Application 20023/1981. However, problems persist when attempting to indwell a desired length of a lengthy catheter into a blood vessel while maintaining sterile conditions.

After the placement of a catheter into the blood vessel with a conventional placement unit, it is impossible to remove the front portion of an insertion means and a cannulated needle from the catheter thus inserted. Accordingly, it is necessary to draw blood-stained insertion means and cannulated needle toward the hands of the medical user so as to fit the same to parts of a base of the catheter, which if viewed by the patient, inevitably makes the patient anxious and uncomfortable.

The above-mentioned insertion means of a conventional placement unit is constituted in a stainless tube, which is formed by insertion molding, a molding operation that is troublesome. Furthermore, a tubular sheath of the introducer unit is made of hard polyethylene, and as a result, there is danger that the sliding portion of the hard sheath tube will be worn away and produce fine powders which could eaily enter the body after having been stuck to the catheter. Therefore, the insertion means of the conventional unit should be made of a fine metal in order to slide smoothly on the sheath tube by reducing sliding resistance. The sliding resistance is an important factor to be considered, when inserting the catheter within the sheath tube, because the resistance between the front portion of the catheter and the blood vessel can only be sensed indirectly in an actual operation. Accordingly, the likelihood of the catheter being forced into the blood vessel and piercing the wall of the vessel is substantial, especially when the sliding resistance of the catheter in the sheath tube and insertion means is large enough to mask the sliding resistance of the catheter within the blood vessel. Such an accident as the above has frequently occurred unexpectedly.

With the conventional placement unit, it is difficult to confirm the length of the catheter inserted into the blood vessel directly through the insertion means because the conventional sheath tube is semi-transparent and the conventional insertion means is not transparent.

Because the hard tubular parts and blood-stained plastic needle of a conventional placement unit remain on the cathether as described above, they are a hindrance when fixing the catheter onto the skin. Furthermore, because in a conventional placement unit, the catheter and capillary extension tube extending from the catheter end outside the patient for connection of the catheter to a tubing connector following catheter placement are integrally constituted, repeated substitutions of a new adaptor for the adaptor already connected to the extension tube, such as for sterilization of the adaptor, may cause such troubles, such as looseness of an arrangement of the catheter, or cracks in the catheter end.

The length of a conventional catheter extending outside the body depends upon the extent to which the catheter is inserted into the blood vessel. Accordingly, it is often necessary to form the excess catheter into a loop.

In carrying out the insertion of the catheter into the blood vessel by means of a film or bag method, two kinds of manual operation are required: hauling in, and pulling back.

SUMMARY OF THE INVENTION

An object of the present invention is to provide a disposable indwelling catheter placement unit for more easily inserting a catheter into the blood vessel up to a desired depth under sterile conditions, and to overcome the conventional defects described above.

The above-mentioned object can be achieved by providing a disposable indwelling catheter placement unit having a catheter for insertion into a blood vessel which comprises a transparent plastic catheter having means for indicating a depth to which the catheter has been inserted, in the form of graduations thereon and being contained slidably free within a transparent plastic tubular sheath having a slit line thereon, a transparent inserter, or insertion means, mounting a transparent plastic inner tube therein and further fitting said inner tube to said means at the front portion thereof, and said sheath and insertion means being allowed to release from a space between the inner tube and insertion means by pushing said sheath tube frontward with the fingers while holding it with other fingers so as to place the catheter only into the blood vessel up to a desired depth therein, while maintaining sterility of the catheter.

BRIEF DESCRIPTION OF THE DRAWINGS

FIG. 1 is an explanatory view of a dividable insertion means in its divided state according to the present invention.

FIG. 2 is an explanatory view of the insertion means illustrated in FIG. 1 fitted to a sheath tube, the inside of which is partially seen.

FIG. 4 is an explanatory view of an insertion means employed in the second embodiment according to the present invention wherein said means is fitted to a sheath tube through which a catheter is inserted slidably free.

FIG. 5 is an explanatory view of a connector, provided with a wing, accordingto the present invention.

DESCRIPTION OF THE PREFERRED EMBODIMENT

Figure 3:
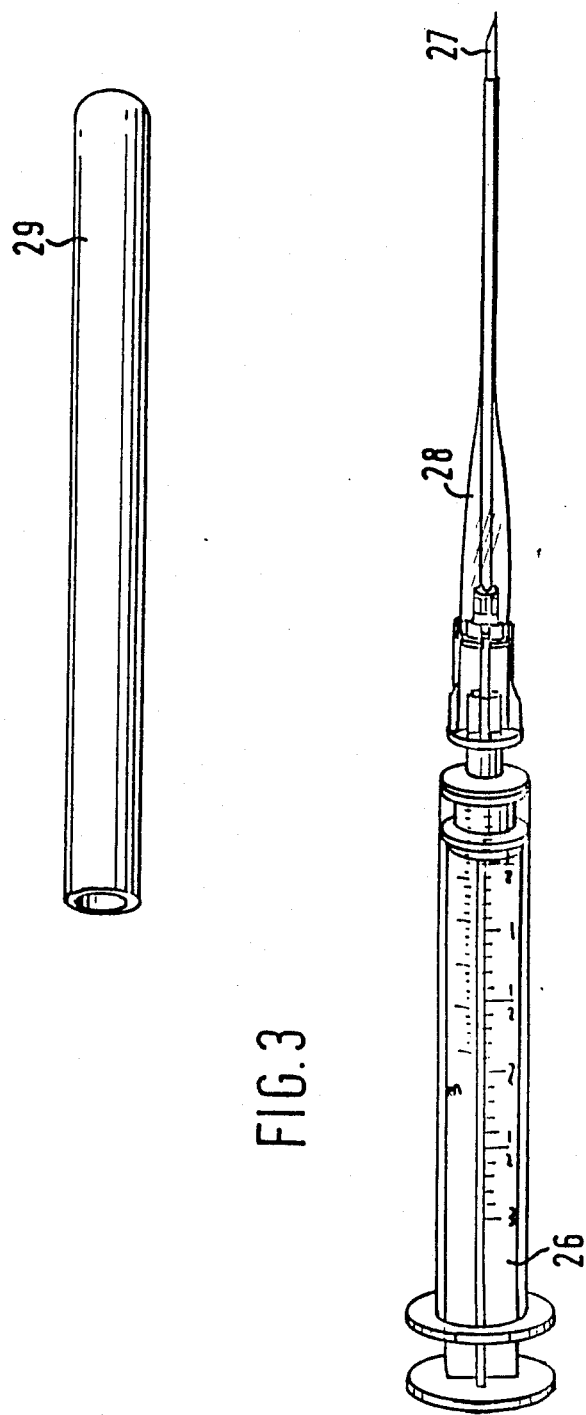
FIG. 3 is a view showing each constitutional element of a syringe provided with a cannulated needle according to the present invention.

Hereinafter, two embodiments of a disposable indwelling catheter placement unit, having a catheter for insertion into the blood vessel according to the present invention will be described with reference to the drawings attached hereto. In each embodiment, each constitutional element of a disposable indwelling cathether placement unit according to the present invention is taken out from a sealed and sterilized container (not illustrated). It is needless to mention that a technical scope of the present invention will not be limited to the following embodiments only.

For the first embodiment, shown in FIGS. 1, 2, 3 and 5, a transparent or semi-transparent plastic inserter or insertion means 1 is dividable into two parts. Referring to FIG. 1, a recess is formed in the means 1 to dispose a transparent or semi-transparent plastic blood check valve 2 therein which is somewhat frontward from a middle protion of the means 1. As shown in FIG. 1, three projections are formed on a divided part of said means 1 and three holes (not illustrated) corresponding to said projections are provided in the other divided part thereof. The insertion means 1 is integrally constituted by fitting the two divided parts to each other. FIG. 2 shows a state wherein said insertion means 1 is fitted to a transparent plastic sheath 5 in which a catheter 4 is freely slidably contained. In this case, it is noted that the catheter only is freely slidably inserted into the check valve 2, and the sheath tube 5 is constituted to be dividable along a slit line 6 formed therein. That is to say, the catheter 4 and sheath tube 5 are in a separated state at each front portion thereof (as shown in FIG. 4) and the sheath tube is in the shape of a circle in section. It is made of an appropriate elastic transparent plastic material. The slit line 6 formed on the sheath tube 5 is always kept closed, so that the catheter 4 inserted into the sheath tube 5 is not exposed even when the sheath tube 5 is bent.

Furthermore, the outer diameter of the catheter 4 is relatively small, i.e. less than 3 m/m and may be molded to a 16 gauge so that it may be inserted into the blood vessel softly and smoothly without causing any flextion thereof. Thus, in placing the catheter into the blood vessel for a long time, particularly in the vicinity of the heart, the catheter, as above described, is advantageously employed since it avoids damaging the blood vessel as a result of catheter movement within the blood vessels.

Next, an inserting operation of the catheter into the blood vessel by employing the unit according to the present invention will be described hereinafter.

Employing a conventional manner at first, a cap 7 of the insertion means 1 is taken off and then a cap 7' of a cannulated needle 8 as shown in FIG. 3 is also taken off. The blood vessel is then pierced by the cannulated needle 8 which includes a metallic needle 11 fixed to a syringe tube 10 within a transparent or semi-trtansparent plastic cannula 9. After having confirmed that needle 11 has pierced the desired blood vessel, the cannula 9 is pushed frontward within the blood vessel while holding metallic needle 11 with the fingers.

In the remainder of the procedure according to the invention, a front portion 12 of the insertion means 1 is then firmly fixed to a funnel or hub portion 13 of the cannula, thereby pushing the sheath tube 5 forward slowly while holding the cannula unmovable by other fingers. Thus, the catheter 4 is also advanced with the forward movement of the sheath tube, so that the catheter may be inserted into the blood vessel. At that time, the sheath tube 5 is released out of an upper part or side of insertion means 1. The catheter 4 may also be advanced in the same manner as above described by pulling the front portion of the sheath tube forwardly with a manual operation instead of pushing the sheath tube forward as above described. As a result, such problems that occur when employing a conventional unit can not occur with the present device.

When the catheter is inserted to the desired depth as indicated by graduations 14 on the catheter 4, the dividable insertion means 1 is manually divided into two parts, so as to release the same from the sheath tube 5. Then the cannula 9 is also carefully released in such manner that the position of the inserted catheter will not be changed. Thereafter, a capillary metallic extension tube 16 (FIG. 5) mounted at a front portion of a connector 15 near a wing 17 on the connector 15, is connected to the catheter 4. The wing 17 may be, when occasion demands, attached to the skin by means of a tape or by means of a suture through an aperture of suitable size (not illustrated) in the wing 17.

In such operation as above, a cap 7' of said connector 15 is taken off so as to connect the same to a dropper (not illustrated), thereby carrying out the necessary treatment. After having finished the treatment, each of the constitutional elements except the catheter may be discarded.

The extension tube 16 and the connector 15 are separately constituted. Accordingly, such conventional trouble as looseness or cracking as above described in substituting adaptors can easily be avoided by exchanging the connector 15 with the wing 17. Furthermore, a protective tube or cover 17' is also arranged in order to protect the extension tube 16 from damage, even when it is grasped by a forceps.

The length of the catheter extending outside of the body depends upon the position of the catheter within the blood vessel. However, it is possible to connect the catheter to the connector 15 by cutting the unnecessary or excess length of the catheter extending the outside of the body to a suitable length by means of a scissors. Thus, it is not necessary to make the extending or excess portion thereof into a loop as often seen in employing a conventional catheter.

A second embodiment according to the present invention will be described with reference to FIG. 4. Like numerical references are used in this Figure for like corresponding parts described in the first embodiment.

Instead of the dividable insertion means 1 as described in the above embodiment, FIG. 4 shows a transparent plastic insertion means 1' fitted to a sheath tube 5 in a manner that only the catheter 4 is slidably inserted into the sheath tube 5. A slit line 6 is also provided on the sheath tube as in the first embodiment. The catheter 4 freely slidably inserted into an inner tube 18 mount within said insertion means 1'.

After fitting the front portion 12 of the insertion means 1' into a funnel portion 13 of the cannula 9, the catheter is inserted into the blood vessel up to a desired depth therein as in the case of the above-mentioned embodiment. Thereafter the sheath tube 5 is pushed forward with fingers while holding the means 1' with the other fingers, thereby releasing sheath tube 5 only from a space 19 formed between inner tube 18 and the insertion means 1', so that the catheter only may be placed into the blood vessel up to a desired depth with sterility. Thus, insertion means 1' may be easily released from the sheath tube. Thereafter, the connector 15 is connected to the catheter 4 and then connected to a dropper (not illustrated), and following treatment, each of the constitutional elements except the catheter may be discarded, as with the first embodiment.

As is clear from the above-mentioned embodiments, a disposable indwelling catheter placement unit for inserting a catheter into the blood vessel in accordance with the present invention can fully avoid the conventional defects as described above in connection with sterility and ease of operation. All the constitutional elements except the catheter may easily be discarded so as not to cause infectious diseases; and since the sheath tube is made of plastics having appropriate rigidity and elasticity, there is no fear that fine particles otherwise produced owing to the wearing away of the slidable portion will enter into the blood vessel. Furthermore, there is no resistance in sliding and inserting the sheath tube on or into the insertion means. Still further, it is possible to easily confirm the insertion length of the catheter into the blood vessel by viewing the depth graduations indicated on the catheter directly through the insertion means.

The matter claimed is:

1. A medical device comprising
   a transparent tubular sheath having longitudinal slit line thereon,
   a transparent plastic catheter having a distal and proximal end and depth graduations thereon for indicating the distance from the distal end thereof, said catheter being freely slidably inserted into said transparent plastic tubular sheath,
   a transparent insertion means having front and back ends and a transparent plastic inner tube mounted within and spaced from the front end of said insertion means,
   said tubular sheath being caused to separate from said catheter along the slit line of said tubular sheath within a space between said inner tube and the front end of said insertion means by moving said tubular sheath forward against the front end of said insertion means with fingers while holding said insertion means with other fingers to allow movement of said catheter into a blood vessel up to a desired depth as indicated by the depth graduations on said catheter and wherein said insertion means is removably attached to a cannula which has previously been inserted into the blood vessel to allow the catheter to pass through the cannula and insertion means.

2. The medical device according to claim 1, wherein said insertion means is made of opaque material and is longitudinally dividable into two substantially mirror image parts.

3. The medical device according to claim 2, wherein said insertion means includes a transparent plastic blood check valve disposed within said inner tube.

4. The medical device according to claim 1, further comprising;
   a connector having front and back ends,
   a capillary extension tube mounted on the front end of said connector for connecting said catheter thereto,
   a protective cover on said extension tube, and
   wherein said connector further includes an elongate wing member mounted thereon to facilitate the attachment of said connector to the skin of a patient.

5. A medical device, comprising:
   a catheter having graduations spaced thereon from a distal end thereof, each of said graduations including an indication means thereon to indicate the distance from a graduation to said catheter distal end,
   a tubular sheath telescoped over said catheter,
   an insertion means slidably telescoped on said catheter for separating the sheath from said catheter responsive to movement of the catheter through said insertion means and for inserting said catheter to a selected depth from within said sheath into a blood vessel while maintaining sterility of said catheter until said catheter enters the blood vessel, and
   a cannula having distal and proximal ends wherein said insertion means attaches to the proximal end thereof and the distal end of said cannula is inserted into a blood vessel to allow the catheter to pass from said insertion means into the blood vessel.

6. A medical device according to claim 5 wherein said insertion means is longitudinally splittable along said catheter for the removal of said insertion means form around said catheter.

7. A medical device according to claim 6, wherein said insertion means is in the form of a catheter inserter having distal and proximal ends and an inner tube extending therethrough for slidably receiving said catheter, said catheter inserter being at least partially transparent to permit visual identification of said graduations on said catheter disposed within said catheter inserter, and said sheath is longitudinally splittable from around said inner tube as the sheath is moved with the catheter through the proximal end of the catheter inserter.

8. A medical device according to claim 6, wherein said tubular sheath is sealed against entry of contaminants along the length thereof and wherein said inserter and sheath are splittable for removal from around said catheter.

9. A medical device according to claim 6, wherein said sheath has a longitudinal slit line over the length thereof and said insertion means has front and back ends and includes an annular space between said inner tube and said front end of said insertion means wherein said sheath is splittable when withdrawn from around said inner tube as said catheter is moved through said insertion means.

10. A method for inserting a catheter into a blood vessel, comprising the steps of:
    piercing a blood vessel with a cannula,
    connecting a front end of an at least partially transparent catheter inserter, through which a catheter is slidably extended, to a hub of said cannula,
    inserting the catheter from a protective sheath around said catheter through said catheter inserter and through the cannula into the blood vessel by holding the connected catheter inserter and cannula with first fingers, grasping the sheath and catheter with other fingers, and pushing the catheter into said catheter inserter, while visually inspecting the catheter inserter to read depth graduation on the catheter,
    stopping the insertion step when a desired depth is indicated by said graduations at said catheter inserter,
    manually dividing the catheter inserter to remove the catheter inserter from around the catheter,
    disconnecting the catheter inserter from the cannula hub,
    withdrawing the cannula from around the catheter and thereafter
    inserting a capillary extension tube into an end of the catheter and
    attaching a connector to the extension tube for attaching other tubing to said catheter.

11. The method of inserting a catheter according to claim 10, with the additional step of the following between the withdrawing and the following inserting steps:

cutting off an excess length of said catheter.

12. The method of inserting a catheter according to claim 10, with the addition of the following step after the last step:

attaching wings on said connector to the patient to fix the position of said catheter.

13. The method of inserting a catheter according to claim 10, wherein the first inserting step also includes the following steps:

splitting the sheath responsive to movement of the sheath and catheter into the catheter inserter, and;

withdrawing the split sheath from around the catheter through an opening in the catheter inserter.

* * * * *